US 12,035,980 B2

(12) United States Patent
Park et al.

(10) Patent No.: US 12,035,980 B2
(45) Date of Patent: Jul. 16, 2024

(54) SYSTEM AND METHOD FOR TRACKING POSITIONING OF MEDICAL INSTRUMENT BY USING AUGMENTED REALITY

(71) Applicant: DECASIGHT CORPORATION, Seoul (KR)

(72) Inventors: Byung Joon Park, Seoul (KR); Soo Ho Choi, Seoul (KR); Tae Hyun Kim, Seoul (KR)

(73) Assignee: DECASIGHT CORPORATION, Seoul (KR)

( * ) Notice: Subject to any disclaimer, the term of this patent is extended or adjusted under 35 U.S.C. 154(b) by 218 days.

(21) Appl. No.: 17/611,755

(22) PCT Filed: Apr. 29, 2020

(86) PCT No.: PCT/KR2020/005685
§ 371 (c)(1),
(2) Date: Nov. 16, 2021

(87) PCT Pub. No.: WO2020/231048
PCT Pub. Date: Nov. 19, 2020

(65) Prior Publication Data
US 2022/0233247 A1 Jul. 28, 2022

(30) Foreign Application Priority Data
May 16, 2019 (KR) .................. 10-2019-0057289

(51) Int. Cl.
A61B 34/20 (2016.01)
A61B 17/34 (2006.01)
A61B 90/00 (2016.01)

(52) U.S. Cl.
CPC .......... A61B 34/20 (2016.02); A61B 17/3403 (2013.01); A61B 90/361 (2016.02);
(Continued)

(58) Field of Classification Search
CPC ................ A61B 17/00; A61B 17/3403; A61B 2034/2057; A61B 2034/2065;
(Continued)

(56) References Cited

U.S. PATENT DOCUMENTS

2008/0009829 A1* 1/2008 Ta ........................... A61F 2/958
604/509
2009/0068620 A1* 3/2009 Knobel .................. A61B 34/20
433/223

(Continued)

FOREIGN PATENT DOCUMENTS

KR 10-2008-0042794 A 5/2008
KR 10-2014-0083913 A 7/2014

OTHER PUBLICATIONS

Office Action of Korean Application No. 10-2019-0057289 dated Oct. 16, 2020.

(Continued)

Primary Examiner — Michael T Rozanski
(74) Attorney, Agent, or Firm — Sughrue Mion, PLLC

(57) ABSTRACT

A medical instrument positioning tracking system includes: a bar-type medical instrument which has a bar shape front end part and an identification segment formed on the rear end part; a tracking multi-camera including a plurality of cameras provided at a plurality of locations so that the identification segment can be photographed in a plurality of time points; a display device for displaying an augmented reality image with the medical instrument as an augmented object and also displaying relevant information including location and angle of the medical instrument; and a control device for acquiring, in real time, a tracking image captured by the tracking multi-camera for every frame, estimating a three-dimensional segment by using the acquired image, estimating the actual three-dimensional positioning of the medical instrument by using the location relationship (Continued)

between a pre-measured location of the medical instrument and the three-dimensional segment, and displaying the estimated three-dimensional positioning information.

22 Claims, 13 Drawing Sheets

(52) U.S. Cl.
CPC ...... *A61B 90/37* (2016.02); *A61B 2034/2057* (2016.02); *A61B 2034/2065* (2016.02); *A61B 2090/365* (2016.02); *A61B 2090/367* (2016.02)

(58) Field of Classification Search
CPC ...... A61B 2034/2068; A61B 2090/365; A61B 2090/367; A61B 2090/372; A61B 2090/3945; A61B 2090/3975; A61B 2090/3983; A61B 34/20; A61B 90/13; A61B 90/361; A61B 90/37
See application file for complete search history.

(56) References Cited

U.S. PATENT DOCUMENTS

| | | | | |
|---|---|---|---|---|
| 2012/0257049 | A1* | 10/2012 | Schnell | G06T 11/001 |
| | | | | 250/336.1 |
| 2015/0320513 | A1* | 11/2015 | Yoon | A61B 6/022 |
| | | | | 382/131 |

OTHER PUBLICATIONS

International Search Report of PCT/KR2020/005685 dated Nov. 3, 2020 [PCT/ISA/210].

* cited by examiner (a)

(b)

(a)

(b)

SYSTEM AND METHOD FOR TRACKING POSITIONING OF MEDICAL INSTRUMENT BY USING AUGMENTED REALITY

CROSS REFERENCE TO RELATED APPLICATIONS

This application is a National Stage of International Application No. PCT/KR2020/005685 filed on Apr. 29, 2020, which claims priority based on Korean Patent Application No. 10-2019-0057289 filed on May 16, 2019, the disclosures of the prior applications are incorporated herein in their entirety.

BACKGROUND OF THE INVENTION

Field of the Invention

The present invention relates to a medical device posture tracking technology, and more particularly, to a technology for providing information by tracking a medical device posture in an operation in which a position and angle of a tip portion of the medical device is important, such as needling, suctioning, and injection.

Description of Related Art

The augmented reality technology is a presentation technology in which a virtual object is superimposed on the real world seen by the user's eyes by projecting a virtual image on an actual image that the user is looking at. According to Ronald Azuma, the augmented reality is defined as first, a combination of a real image and a virtual image, second, interfering in real time, and finally being placed in a three-dimensional space. The augmented reality is different from the virtual reality technique in which the user is immersed in the virtual image and cannot see the real surrounding environment, and it provides better realism and additional information through a mixture of the real environment and virtual objects. This augmented reality technology has been studied mainly in the United States since the late 1990s. Commercialization is being attempted along with the recent spread of smart phones, and various products are being released in the field of games and education.

Recently, researches to apply such virtual reality to the field of medical surgery simulation are being actively conducted.

Medical surgery can be classified into open surgery, minimally invasive surgery (MIS), radiosurgery, and the like. The open surgery refers to an operation in which a medical staff directly sees and touches the part to be treated. As the MIS, also called keyhole surgery, laparoscopic surgery is the most representative. In the laparoscopic surgery, a small hole is made in a necessary part without open surgery, a laparoscope with a special camera and surgical tools are inserted into the patient's body to perform micro-operation by using a laser or the special instrument while observing through the video monitor. Furthermore, radio-surgery refers to surgical treatment performed outside the patient's body with radiation or laser light.

In the medical surgery field, Virtual Endoscopy, Image Guided Surgery, and Preoperative Planning techniques are currently applied as the virtual reality. In Virtual Endoscopy, a surgeon examines a relevant part while virtually exploring the inside of the patient's body received as a volume image through imaging such as magnetic resonance imaging (MRI) or computed tomography (CT) in a virtual space. The endoscopy is most widely applied to surgery for a stomach and a large intestine. The virtual endoscopy is performed in a virtual space where the image quality is not lower than that of the real endoscope, and there is no pain for the patient. Moreover, since the endoscopy can be applied to the inside of blood vessels or cerebral cavities which is difficult to be explored in practice, it is expected to be widely used for diagnosis in the future. Image-Guided Surgery can be said to utilize the augmented reality method rather than virtual reality, and is a technology that allows accurate operation by showing the inside of the area to be operated matching with the actual area. Preoperative Planning is a technology that helps the doctor to plan in advance which method is most effective by classifying, visualizing, and manipulating the patient's organs or tissues in a virtual space before performing the surgical procedure.

As described above, with development of the augmented reality technology, researches for applying the augmented reality to medical care is being conducted worldwide, and attempts for using it as an educational program showing anatomical structures or as a surgical assistant are being made in the art. However, the conventional medical augmented reality technique is limited to implementation of augmented reality based on image tracking using simple visual markers. In the case of a method based on image tracking, image matching is performed by capturing an image and analyzing the captured image. However, in the case of such an image tracking-based method, draping is preceded in medical procedures or surgeries that are basically aseptic and non-contact, and most of the patient's body is covered by a sterile sheet, so that it is difficult to photograph an image to be matched. Therefore, there is a limitation in application of augmented reality. In addition, there is a risk that the image accuracy may be degraded by bleeding or optical reflection.

SUMMARY OF THE INVENTION

In order to address the problems or disadvantages described above, the present invention provides a system and method for tracking a medical device posture based on augmented reality, capable of more robustly estimating the medical device posture.

The object of the present invention is not limited to those described above, and other unmentioned objects would become apparent to those skilled in the art would by reading the following description.

In order to achieve the objects described above, according to an aspect of the present invention, there is provided a medical device posture tracking system comprising: a bar type medical device having a bar shape whose front end has a needle or injection shape and whose rear end has an identification line segment extending in a longitudinal direction of the bar shape; a tracking multi-camera set having a plurality of cameras provided in a plurality of locations to photograph the identification line segment at a plurality of viewpoints; a display unit configured to display an augmented reality image having the bar type medical device as an augmented object and show related information including a position and angle of the bar type medical device; and a controller configured to acquire tracking images captured from the tracking multi-camera set in real time for each frame, estimate a three-dimensional line segment by using the acquired image, estimate an actual three-dimensional posture of the bar type medical device by using the positional relationship between the bar type medical device and the three-dimensional line segment measured in advance, and display the estimated three-dimensional posture information including the position and angle information of the bar type medical device on the display unit as an augmented reality image.

The bar type medical device may have a laser emitting unit for emitting a laser beam at its rear end, and the laser emitting unit may emit the laser beam to form the identification line segment.

The rear end of the bar type medical device may be formed of a transparent material visible from the outside.

The rear end of the bar type medical device may be filled with a medium containing a silver solution or aerogel to make the laser beam visible from the outside.

A tip of the rear end of the bar type medical device may be provided with a blocking portion formed of a non-transmissive material to prevent the laser beam from leaking to the outside.

The tracking multi-camera set may photograph the laser beam.

The display unit may be provided with a rear camera for photographing a rear direction and may display an image photographed from the rear camera and the three-dimensional posture information as an augmented reality image in response to a control of the controller.

The controller may perform a camera calibration operation for measuring a positional relationship between each camera of the tracking multi-camera set in advance.

The controller may perform an image cleaning operation for separating a laser beam from the image photographed from the tracking multi-camera set and removing unnecessary noise.

The controller may perform a two-dimensional optimum line segment search operation for searching for an optimum two-dimensional line segment for each image photographed from each camera by using a statistical line fitting algorithm after the image cleaning operation.

The controller may perform an optimum three-dimensional restoration operation by using information on the two-dimensional line segments and the positional relationship information between each camera of the tracking multi-camera set. For example, the controller may perform a three-dimensional line segment restoration operation by binding information on two-dimensional line segments two by two and restoring a plurality of three-dimensional line segments by using the positional relationship information between each camera of the tracking multi-camera set after the two-dimensional optimum line segment search. The controller may search for an optimum three-dimensional line segment by performing line fitting for information on both endpoints of the restored three-dimensional line segments after the three-dimensional line segment restoration operation.

The controller may estimate a three-dimensional posture of the actual medical device by using a positional relationship between the bar type medical device and the optimum three-dimensional line segment measured in advance.

According to another aspect of the present invention, there is provided a medical device posture tracking method comprising: acquiring tracking images photographed from a tracking multi-camera set in real time for each frame; estimating a three-dimensional line segment by using the acquired image; estimating a three-dimensional posture of the actual bar type medical device by using the positional relationship between the bar type medical device and the three-dimensional line segment measured in advance; and displaying the estimated three-dimensional posture information including the estimated position and angle information of the bar type medical device on the display unit as an augmented reality image.

The bar type medical device may have a laser emitting unit for emitting a laser beam at its rear end, and the laser emitting unit may emit the laser beam to form an identification line segment.

The rear end of the bar type medical device may be formed of a transparent material visible from the outside.

The rear end of the bar type medical device may be filled with a medium containing a silver solution or aerogel to make the laser beam visible from the outside.

A blocking portion formed of a non-transmissive material for preventing the laser beam from leaking to the outside may be provided at a tip of the rear end of the bar type medical device.

The tracking multi-camera set may photograph the laser beam.

The display unit may be provided with a rear camera for photographing a rear direction and may display an image photographed from the rear camera and the three-dimensional posture information as an augmented reality image in response to a control of the controller.

The controller may further perform a camera calibration operation for measuring a positional relationship between each camera of the tracking multi-camera set in advance.

The controller may further perform an image cleaning operation for separating a laser beam from the image captured from the tracking multi-camera set and removing unnecessary noise.

The controller may further perform a two-dimensional optimum line segment search operation for searching for an optimum two-dimensional line segment for each image photographed from each camera by using a statistical line fitting algorithm after the image cleaning operation.

The controller may further perform an optimum three-dimensional restoration operation by using information on the two-dimensional line segments and the positional relationship information between each camera of the tracking multi-camera set. For example, the controller may perform a three-dimensional line segment restoration operation by binding information on two-dimensional line segments two by two and restoring a plurality of three-dimensional line segments by using the positional relationship information between each camera of the tracking multi-camera set after the two-dimensional optimum line segment search. The controller may search for an optimum three-dimensional line segment by performing line fitting for information on both endpoints of the restored three-dimensional line segments after the three-dimensional line segment restoration operation.

The controller may further estimate a three-dimensional posture of the actual medical device by using a positional relationship between the bar type medical device and the optimum three-dimensional line segment measured in advance.

According to the present invention, it is possible to easily estimate information such as a position or angle of the medical device by tracking the posture of the medical device using the augmented reality.

In addition, according to the present invention, it is possible to propose a more robust method for estimating the posture of the medical device by addressing the problems of the square marker tracking scheme of the prior art.

Furthermore, according to the present invention, it is possible to allow a medical staff who uses the medical device to more intuitively utilize the medical device by visualizing and presenting the medical device posture tracking on the basis of the augmented reality technology. In particular, the present invention can be very usefully utilized in a laparoscopic surgery, a thoracoscopic surgery, or the like based on a needle or injection.

DETAILED DESCRIPTION OF THE INVENTION

Figure 1:
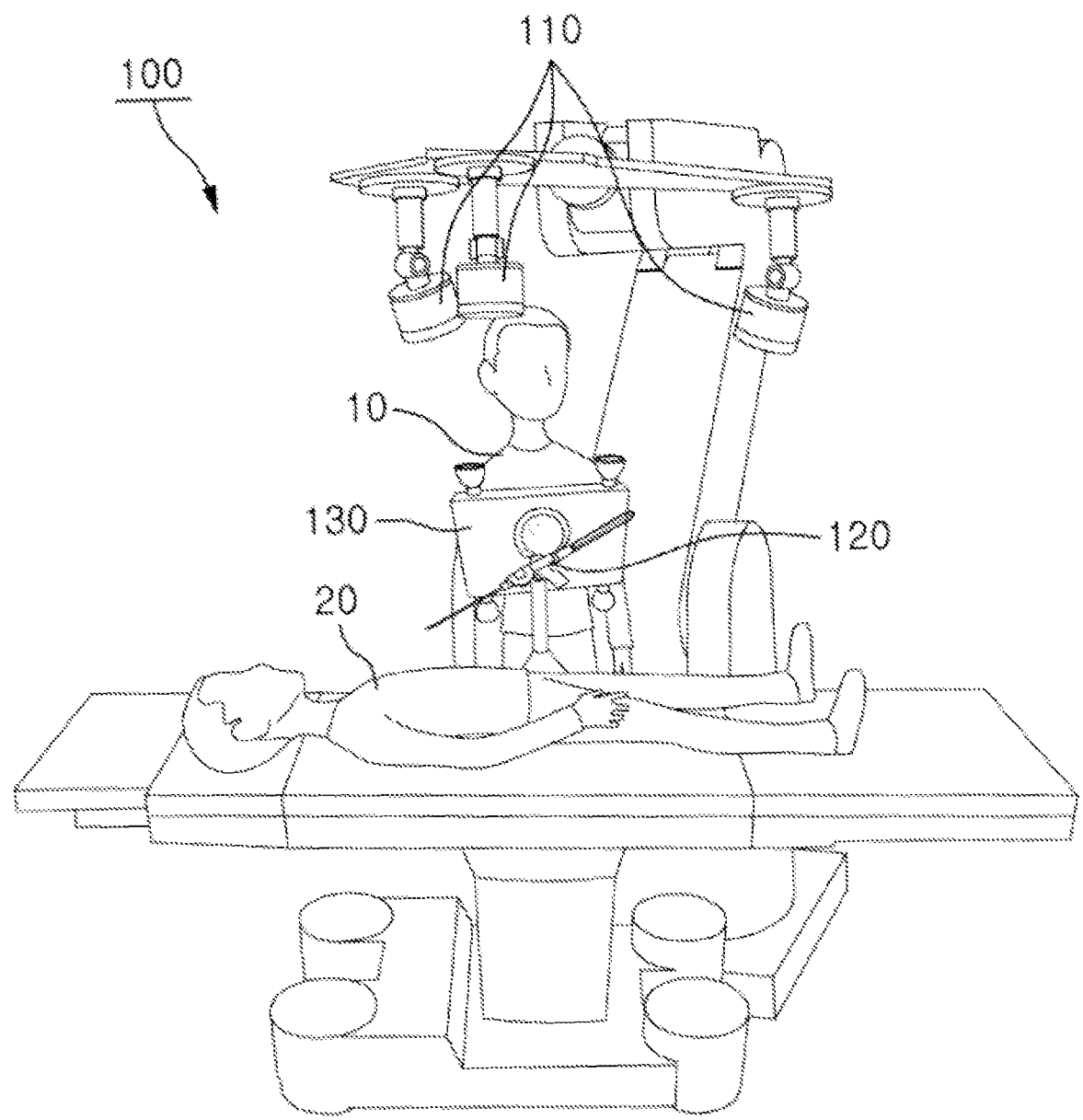
FIG. 1 schematically illustrates a medical device posture tracking system according to an embodiment of the present invention.

According to the present invention, there is provided a medical device posture tracking system comprising: a bar type medical device having a bar shape whose front end has a needle or injection shape and whose rear end has an identification line segment extending in a longitudinal direction of the bar shape; a tracking multi-camera set having a plurality of cameras provided in a plurality of locations to photograph the identification line segment at a plurality of viewpoints; a display unit configured to display an augmented reality image having the bar type medical device as an augmented object and show related information including a position and angle of the bar type medical device; and a controller configured to acquire tracking images captured from the tracking multi-camera set in real time for each frame, estimate a three-dimensional line segment by using the acquired image, estimate a three-dimensional posture of the actual bar type medical device by using the positional relationship between the bar type medical device and the three-dimensional line segment measured in advance, and display the estimated three-dimensional posture information including the position and angle information of the bar type medical device on the display unit as an augmented reality image.

Hereinafter, preferred embodiments of the invention will be described in detail with reference to the accompanying drawings. It is noted that like reference numerals denote like elements throughout overall drawings. In addition, descriptions of well-known apparatus and methods may be omitted so as to not obscure the description of the representative embodiments, and such methods and apparatus are clearly within the scope and spirit of the present disclosure. The terminology used herein is only for the purpose of describing particular embodiments and is not intended to limit the invention. As used herein, the singular forms "a," "an," and "the" may be intended to include the plural forms as well, unless the context clearly indicates otherwise. It is further to be noted that, as used herein, the terms "comprises," "comprising," "include," and "including" indicate the presence of stated features, integers, steps, operations, units, and/or components, but do not preclude the presence or addition of one or more other features, integers, steps, operations, units, and/or components, and/or combination thereof Unless specified otherwise, all terminologies used herein including technical or scientific terminologies have the same meanings as those generally appreciated by a person ordinarily skill in the art to which the present invention pertains. Terminologies defined in typical dictionaries should be construed to have meanings matching those described in the context of the related art, and should not be construed as being abnormal or excessively formal unless defined apparently herein.

The present invention will now be described with reference to the accompanying drawings, in which like reference numerals denote like elements throughout the entire specification, and they will not be repeatedly described intentionally. In the following description, any specific word or sentence for the related art will not be provided for simplicity purposes if it unnecessarily obscures the subject matter of the invention.

FIG. 1 schematically illustrates a medical device posture tracking system according to an embodiment of the present invention. In FIG. 1, it is assumed that a medical staff 10 performs an operation on a patient 20 by way of example.

Referring to FIG. 1, the medical device posture tracking system has a tracking multi-camera set 110, a bar type medical device 120, a display unit 130, and a controller (not shown).

The tracking multi-camera set 110 includes a plurality of cameras installed in a plurality of places so as to photograph the identification line segments formed on the bar type medical device 120 at a plurality of time points.

The concept of the bar type medical device 120 includes various medical devices such as a needle, injection, a laparoscopic surgical instrument, and a thoracoscopic surgical instrument. The front end has a bar shape including a needle or injection shape, and the rear end has an identification line segment formed in the longitudinal direction of the bar shape.

The display unit 130 is a device that displays the bar type medical device 120 and the inside of the body of the patient 20 as augmented objects in an augmented reality space on an augmented reality image, as well as related information including position and angle data of the bar type medical device 120.

The controller (not shown) acquires the tracking images captured by the tracking multi-camera set 110 in real time for every frame, and tracks the three-dimensional line segment by using the acquired image. In addition, the controller estimates the three-dimensional posture of the actual bar type medical device on the basis of a positional relationship between the position of the bar type medical device 120 and the three-dimensional line segment measured in advance. Furthermore, the three-dimensional posture information including the estimated position and angle information of the bar type medical device is displayed on the display unit 130 as an augmented reality image.

According to the present invention, the tracking multi-camera set 110 may photograph the laser beam formed on the bar type medical device 120 to track the three-dimensional line segment.

Figure 2:
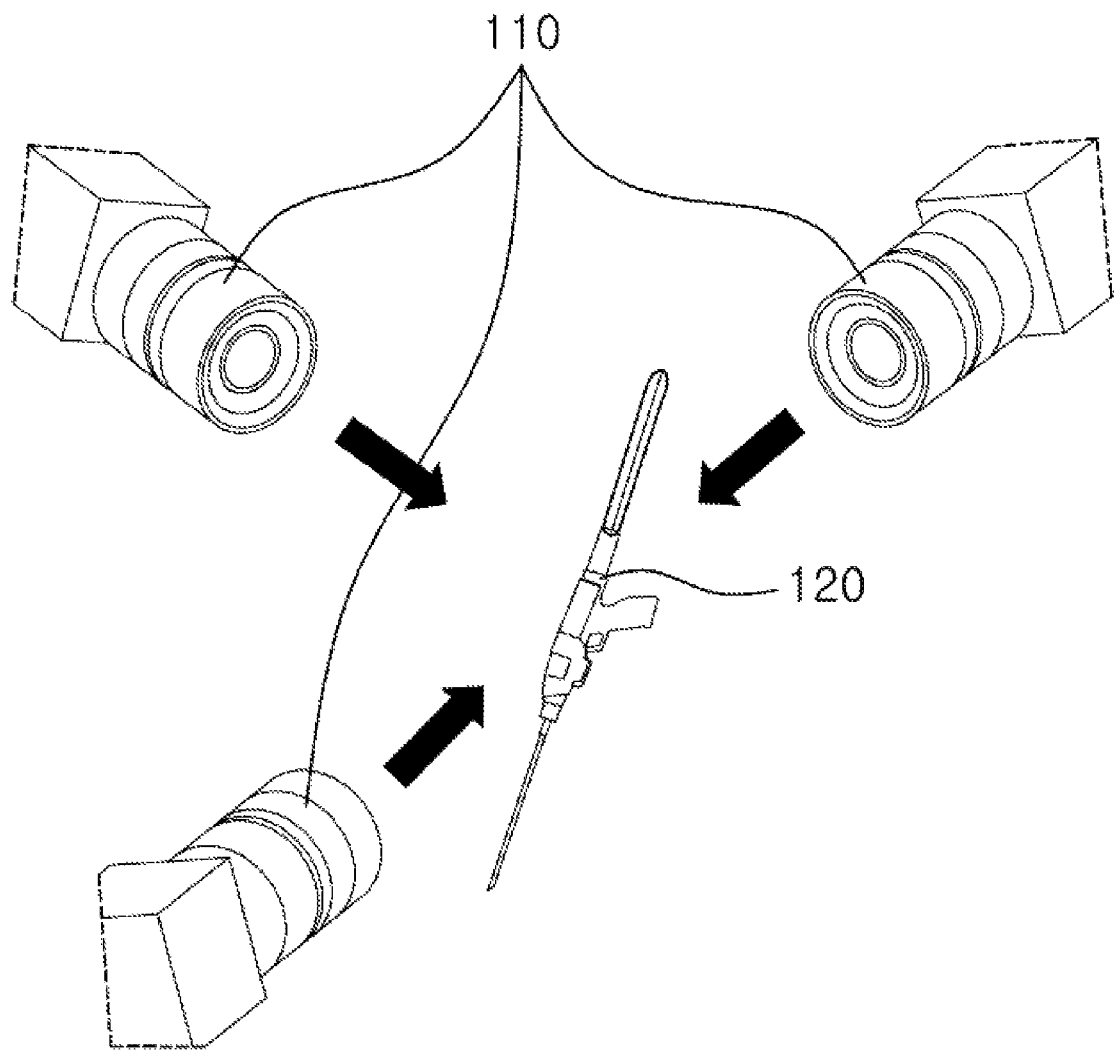
FIG. 2 illustrates a multiple camera setup for tracking according to an embodiment of the present invention.

FIG. 2 illustrates the tracking multi-camera set according to an embodiment of the present invention.

Referring to FIG. 2, the tracking multi-camera set 110 according to the present invention has at least two cameras to photograph the laser beam formed in the bar type medical device 120 at multiple viewpoints. Preferably, the cameras may be arranged in consideration of the angle of view so as not to cause a blind spot as much as possible. According to the present invention, it is preferable that three to four or more cameras are arranged to form a plane. As more cameras are provided, an error in posture estimation using the laser beam can be reduced more effectively.

According to the present invention, the line segment for identifying the bar type medical device 120 may be implemented in various ways. For example, the identification line segment may be implemented using a special paint on the bar type medical device 120. However, since the present invention is utilized in medical fields such as treatment and surgery related to the human body and life, precise measurement is necessary. Therefore, according to the present invention, it is preferable to implement the identification line segment of the bar type medical device 120 using a laser beam. It is known that the laser beam can implement a very thin straight line segment.

According to the present invention, the bar type medical device 120 is provided with a laser emitting unit for emitting a laser beam at the rear end so as to form an identification line segment by emitting a laser beam from the laser emitting unit.

Figure 3:
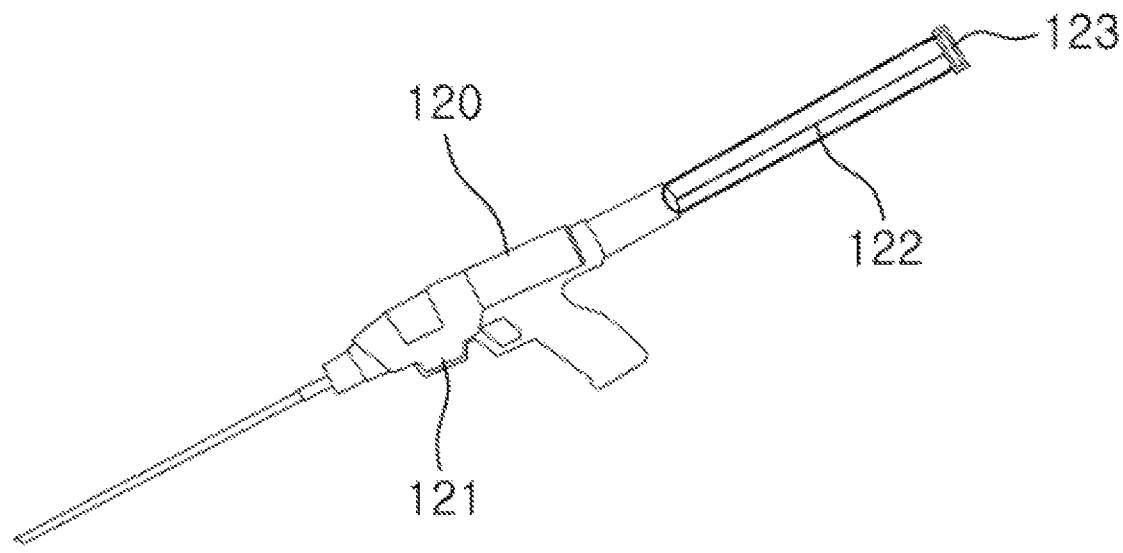
FIG. 3 illustrates a bar type medical device according to an embodiment of the present invention.
Figure 3:
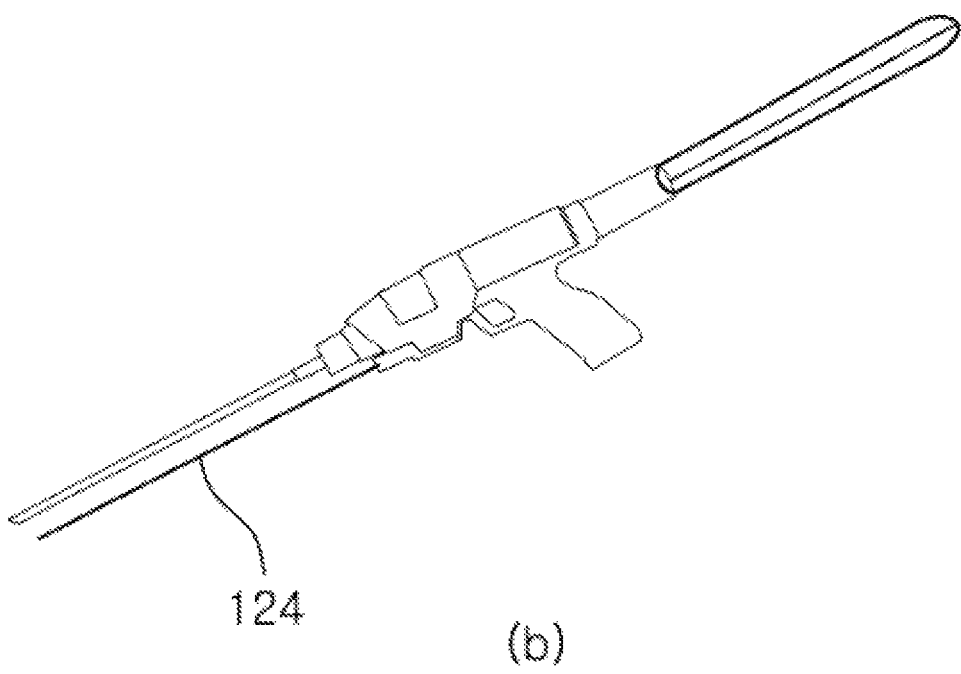

FIG. 3 illustrates the bar type medical device according to an embodiment of the present invention.

Referring to FIG. 3(a), according to an embodiment of the present invention, a glass tube (formed of various types of materials such as transparent plastic) having a laser emitting unit may be attached to the rear end of the main body 121 of the bar type medical device 120.

According to the present invention, the rear end of the bar type medical device 120 may be formed of a transparent material to make the laser beam 122 visible from the outside.

The rear end of the bar type medical device 120 may be filled with a medium containing a silver solution (colloidal silver) or aerogel to make the laser beam clearly visible from the outside.

The tip of the rear end of the bar type medical device 120 may be provided with a blocking portion formed of a non-transmissive material 123 to prevent the laser beam from leaking to the outside. When the blocking portion 123 is not formed at the tip of the rear end, the laser beam may leak to the outside through the transparent glass tube. Therefore, according to the present invention, the blocking portion 123 may be formed by attaching a tape of a non-transmissive material such as carbon or graphite to the tip of the rear end so as to prevent the laser beam from leaking to the outside of the glass tube.

According to the present invention, the laser beam used in the bar type medical device 120 preferably uses a relatively strong laser in consideration of the specificity and visibility of the medical environment. For example, a laser beam having a power of 100 mW or stronger may be used.

For the posture (position and angle) estimation of the bar type medical device 120, the three-dimensional posture is estimated by using the positional relationship between the bar type medical device and the laser beam measured in advance. For this purpose, for example, the laser beam line segment and the needle of the bar type medical device may have the same angle and length while the body portion of the medical device is interposed therebetween. However, without limiting to a case where the length of the laser beam line segment and the length of the needle of the bar type medical device have the same length, the lengths may be set to have a predetermined ratio, and the length of the laser beam line segment may be longer than the length of the needle. Depending on applications, the bar type medical device 120 may be configured to adjust the length of the laser beam line segment. When the length of the laser beam line segment is set to be long, the posture of the needle of the bar type medical device can be more precisely estimated. In this configuration, when the position and length of the laser beam line segment are precisely estimated, the position and length of the needle of the bar type medical device can be estimated automatically and accurately.

Referring to FIG. 3(b), a laser beam may be additionally emitted in a direction invasive to the patient by adding a laser emitting device under the needle of the bar type medical device 120. The distance that the emitted laser beam 124 reaches to the patient's skin surface is automatically measured, so that the length of the needle inserted into the patient's body can be more precisely estimated. For example, the length of the needle inserted into the patient's body can be automatically estimated by subtracting the patient's skin surface arrival distance of the laser beam 124 from the entire length of the needle.

Figure 4:
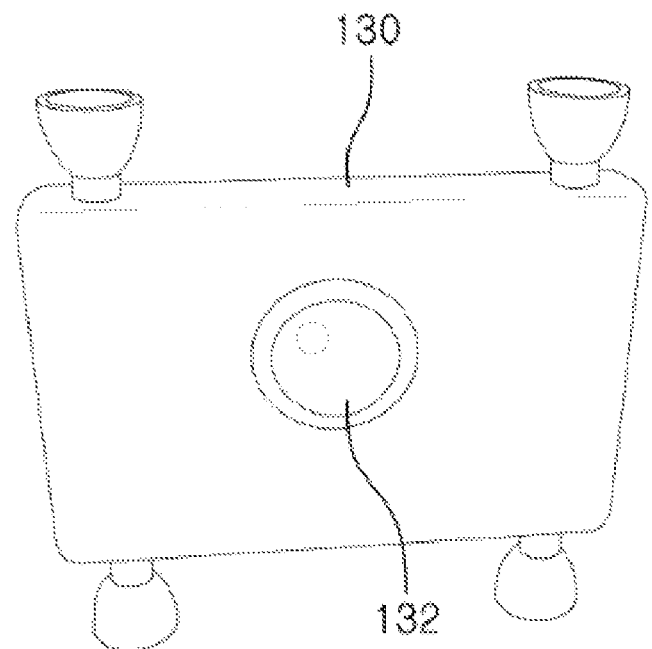
FIG. 4 illustrates a display unit according to an embodiment of the present invention.
Figure 4:
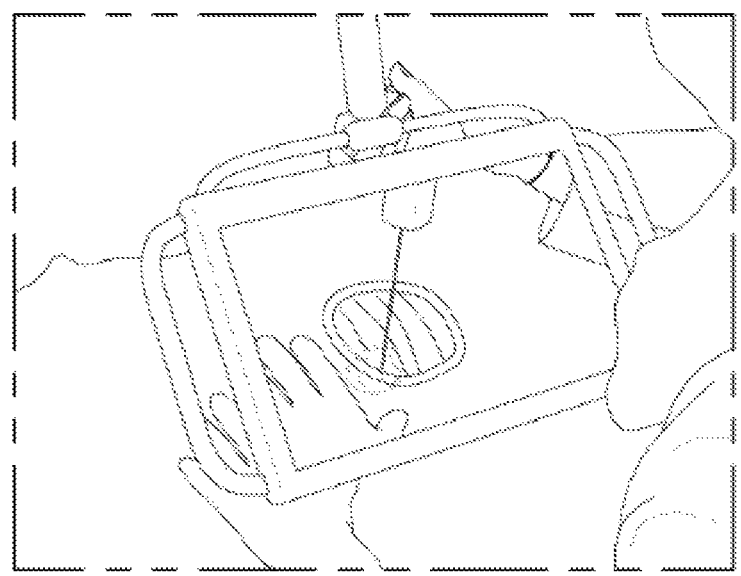

FIG. 4 illustrates a display unit according to an embodiment of the present invention.

Referring to FIG. 4, the display unit 130 is provided with a rear camera 132 for photographing the rear direction, and the image photographed from the rear camera 132 and three-dimensional posture information may be displayed as the augmented reality image in response to a control of the controller. FIG. 4(a) illustrates the front side of the display unit 130 through which the medical staff 10 can watch the augmented reality screen.

Figure 5:
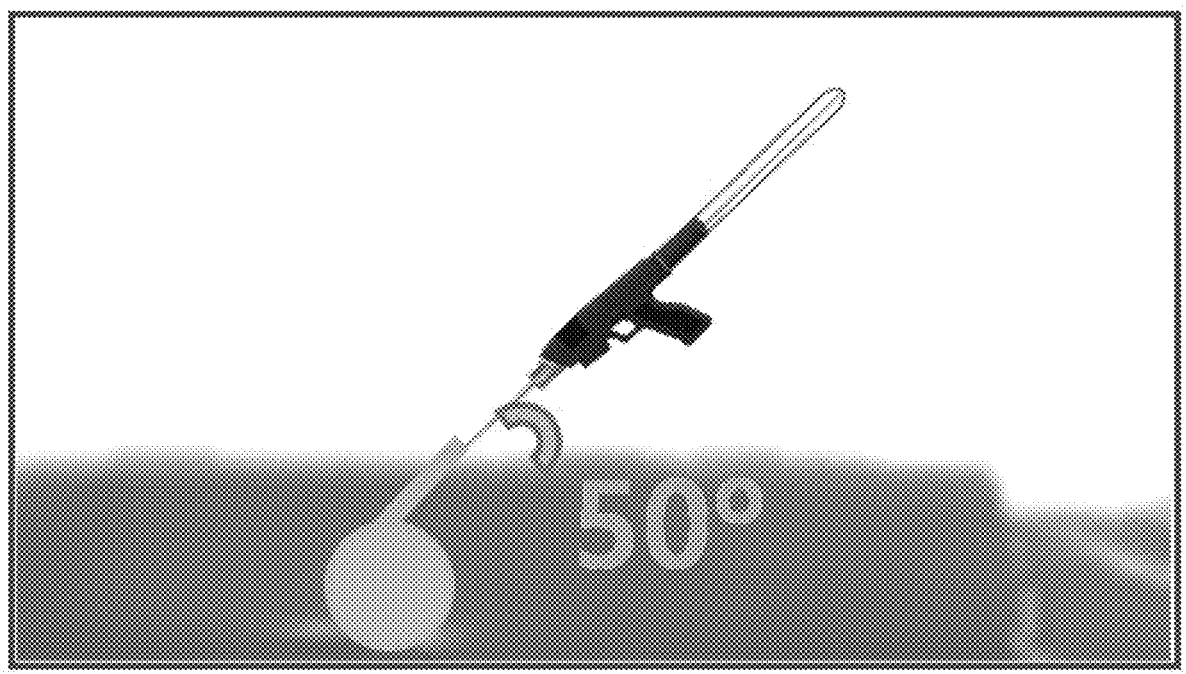
FIG. 5 illustrates an exemplary screen of the display unit according to an embodiment of the present invention.

FIG. 5 illustrates an exemplary screen display of the display unit according to an embodiment of the present invention.

Referring to FIG. 5, an augmented reality image displayed on the display unit 130 is illustrated.

According to the present invention, the controller may perform a camera calibration operation to determine in advance the positional relationship of each camera of the tracking multi-camera set 110.

In addition, the controller may perform an image cleaning operation for separating the laser beam from the image acquired from the tracking multi-camera set 110 and removing unnecessary noise.

After the image cleaning operation, the controller may perform a two-dimensional optimum line segment search operation to search for an optimal two-dimensional line segment for each image captured by each camera using a statistical line fitting algorithm.

After the two-dimensional optimum line segment search, the controller may perform a three-dimensional optimum line segment restoration operation by using information on a plurality of two-dimensional line segments and positional relationship information between each camera of the tracking multi-camera set 110. For example, after the two-dimensional optimum line segment search, the controller may perform a three-dimensional line segment restoration operation by binding two-dimensional line segments two by two and restoring a plurality of three-dimensional line segments using the positional relationship information between each camera of the tracking multi-camera set 110. Then, after the three-dimensional line segment restoration operation, the controller may search for the optimum three-dimensional line segment by performing line-fitting for the information on both endpoints of the restored three-dimensional line segments.

The controller may estimate the three-dimensional posture of the actual medical device using the positional relationship between the bar type medical device and the optimum three-dimensional line segment measured in advance.

Figure 6:
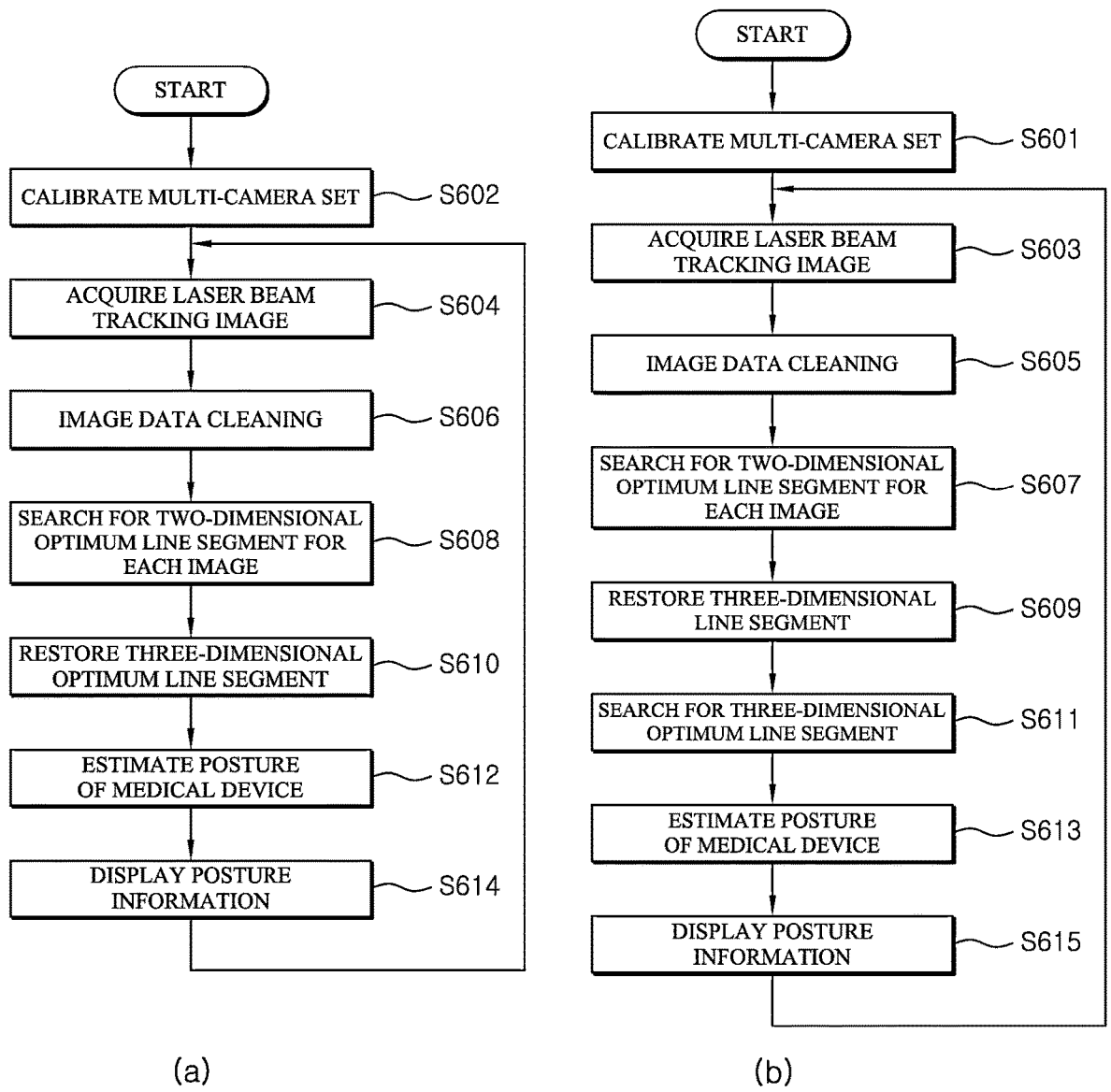
FIG. 6 is a flow chart illustrating a medical device posture tracking method according to an embodiment of the present invention.

FIG. 6 is a flowchart illustrating a medical device posture tracking method according to an embodiment of the present invention.

Referring to FIG. 6(*a*), in the medical device posture tracking system according to the present invention, the controller performs a camera calibration operation for measuring the positional relationship of each camera of the tracking multi-camera set 110 in advance (S602).

The controller acquires the tracking image captured by the tracking multi-camera set 110 in real time for every frame (S604).

Then, the controller separates the laser beam from the image acquired from the tracking multi-camera set 110, and performs an image cleaning operation to remove unnecessary noise (S606).

After the image cleaning operation, the controller performs a two-dimensional optimum line segment search operation for searching for an optimum two-dimensional line segment for each image captured from each camera using a statistical line fitting algorithm (S608).

After the two-dimensional optimum line segment search, the controller performs an optimum three-dimensional line segment restoration operation using information on a plurality of two-dimensional line segments and positional relationship information between each camera of the tracking multi-camera set 110 (S610).

Then, the controller estimates the three-dimensional posture of the actual medical device using the positional relationship between the bar type medical device and the optimum three-dimensional line segment measured in advance (S612).

Then, the controller displays three-dimensional posture information including the estimated position and angle information of the bar type medical device as an augmented reality image on the display unit 130 (S614).

In step S602, for three-dimensional restoration of the laser beam, a camera calibration process is performed for measuring the positional relationship between the cameras of the tracking multi-camera set 110 in advance. In this case, the camera calibration process uses various methods well known in the art. For example, the positional relationship of the cameras is measured with the minimum error by using already disclosed methods such as Bo Li's and Tomas Svoboda's methods.

FIG. 6(*b*) shows a medical device posture tracking method for exemplarily explaining the optimum three-dimensional line segment restoration operation of FIG. 6(*a*). Referring to FIG. 6(*b*), in the posture tracking method of the medical device posture tracking system according to the present invention, the controller performs a camera calibration operation for measuring the positional relationship between each camera of the tracking multi-camera set 110 in advance (S601).

Then, the controller acquires the tracking image captured from the tracking multi-camera set 110 in real time for every frame (S603).

Then, the controller separates the laser beam from the image acquired from the tracking multi-camera set 110, and performs an image cleaning operation to remove unnecessary noise (S605).

After the image cleaning operation, the controller performs a two-dimensional optimum line segment search operation for searching for an optimum two-dimensional line segment for each image captured from each camera using a statistical line fitting algorithm (S607).

After the two-dimensional optimum line segment search, the controller performs an optimum three-dimensional line segment restoration operation using information on a plurality of two-dimensional line segments and the positional relationship information between each camera of the tracking multi-camera set 110 (S609 and S611). For example, after the two-dimensional optimum line segment search, the controller binds information on the two-dimensional line segments two by two and performs the three-dimensional line segment restoration operation for restoring a plurality of three-dimensional line segments using the positional relationship information between each camera of the tracking multi-camera set (S609). After the three-dimensional line segment restoration operation, the controller searches for an optimum three-dimensional line segment by line-fitting the information on both endpoints of the restored three-dimensional line segments (S611).

Then, the controller estimates the three-dimensional posture of the actual medical device using the positional relationship between the bar type medical device and the optimum three-dimensional line segment measured in advance (S613).

Then, the controller displays three-dimensional posture information including the estimated position and angle information of the bar type medical device as an augmented reality image on the display unit 130 (S615).

In step S601, for three-dimensional restoration of the laser beam, a camera calibration process for measuring a positional relationship between the cameras of the tracking multi-camera set 110 is performed. In this case, the camera calibration process uses various methods well known in the art. For example, the positional relationship of the cameras is measured with the minimum error by using already disclosed methods such as Bo Li's and Tomas Svoboda's methods.

Figure 7:
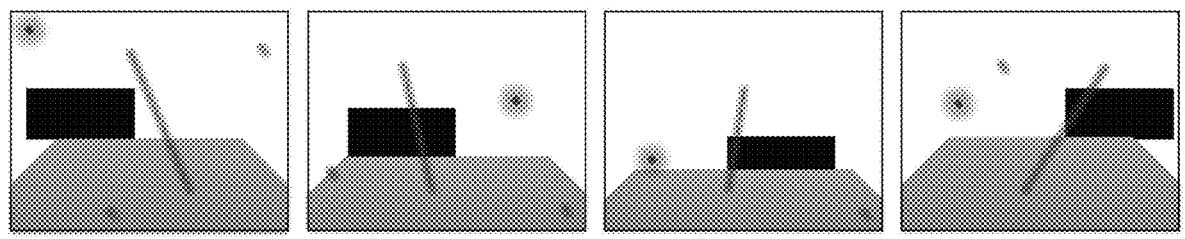
FIG. 7 is a diagram for explaining a laser beam tracking image capture operation according to an embodiment of the present invention.

FIG. 7 is a diagram for explaining a laser beam tracking image capturing operation according to an embodiment of the present invention.

In FIG. 7, the tracking multi-camera set 110 exemplarily has four cameras, and images captured by each camera are shown as four image screens.

Referring to FIG. 7, in step S603, the controller acquires all images captured by each camera in real time for every frame. For example, the images can be acquired via various media such as USB and networks that are not affected by the bandwidth of individual cameras.

Figure 8:
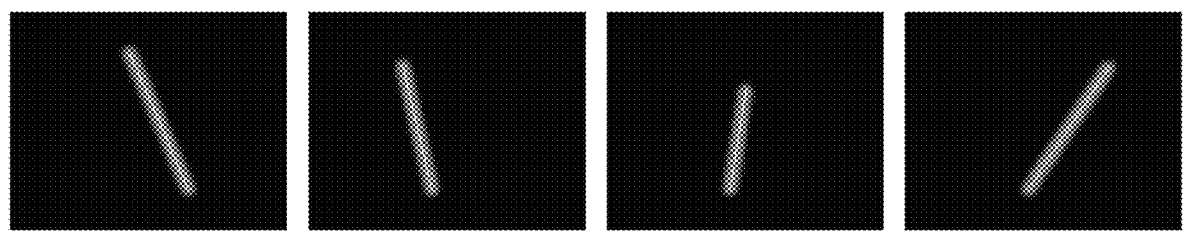
FIG. 8 is a diagram for explaining an image processing operation according to an embodiment of the present invention.

FIG. 8 is a diagram for explaining an image cleaning operation according to an embodiment of the present invention.

Referring to FIG. 8, in the image cleaning operation of step S605, a laser color range is separated for each camera from the image acquired in step S603, and unnecessary noise smaller than a predetermined area is removed as much as possible.

Figure 9:
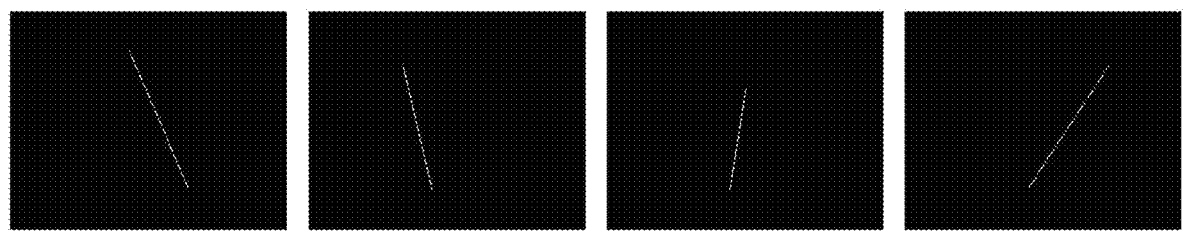
FIG. 9 is a diagram for explaining a two-dimensional optimum line segment search operation according to an embodiment of the present invention.

FIG. 9 is a diagram for explaining the two-dimensional optimum line segment search operation according to an embodiment of the present invention.

Referring to FIG. 9, in the two-dimensional optimum line segment search operation for each image in step S607, an optimum line segment is searched on the basis of a statistically robust line fitting algorithm. In this case, as the line fitting algorithm, any algorithm well known in the art, such as Inui, Meer, and Rousseeuw may be employed.

Figure 10:
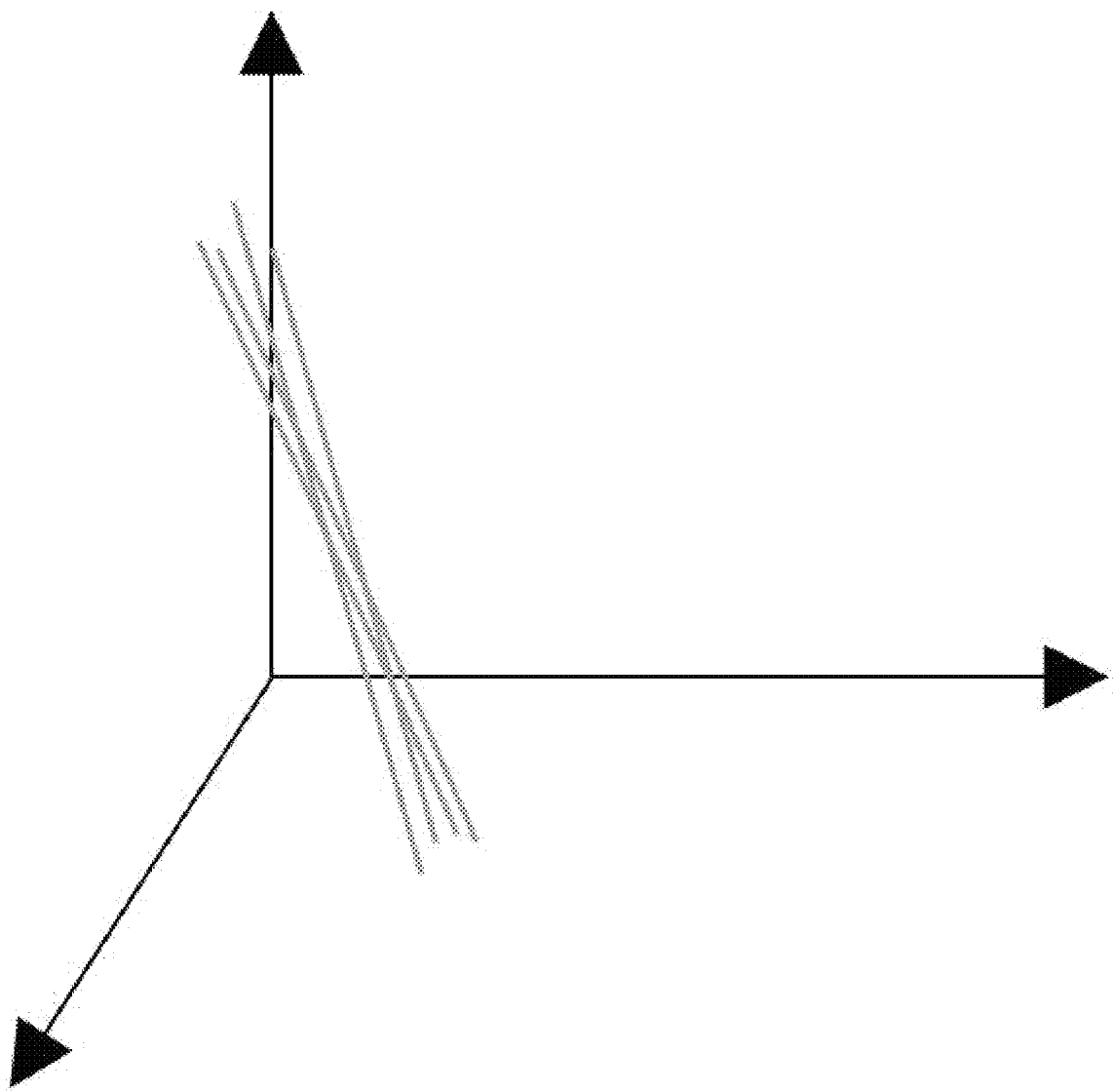
FIG. 10 is a diagram for explaining a three-dimensional line segment restoration operation according to an embodiment of the present invention.
Figure 11:
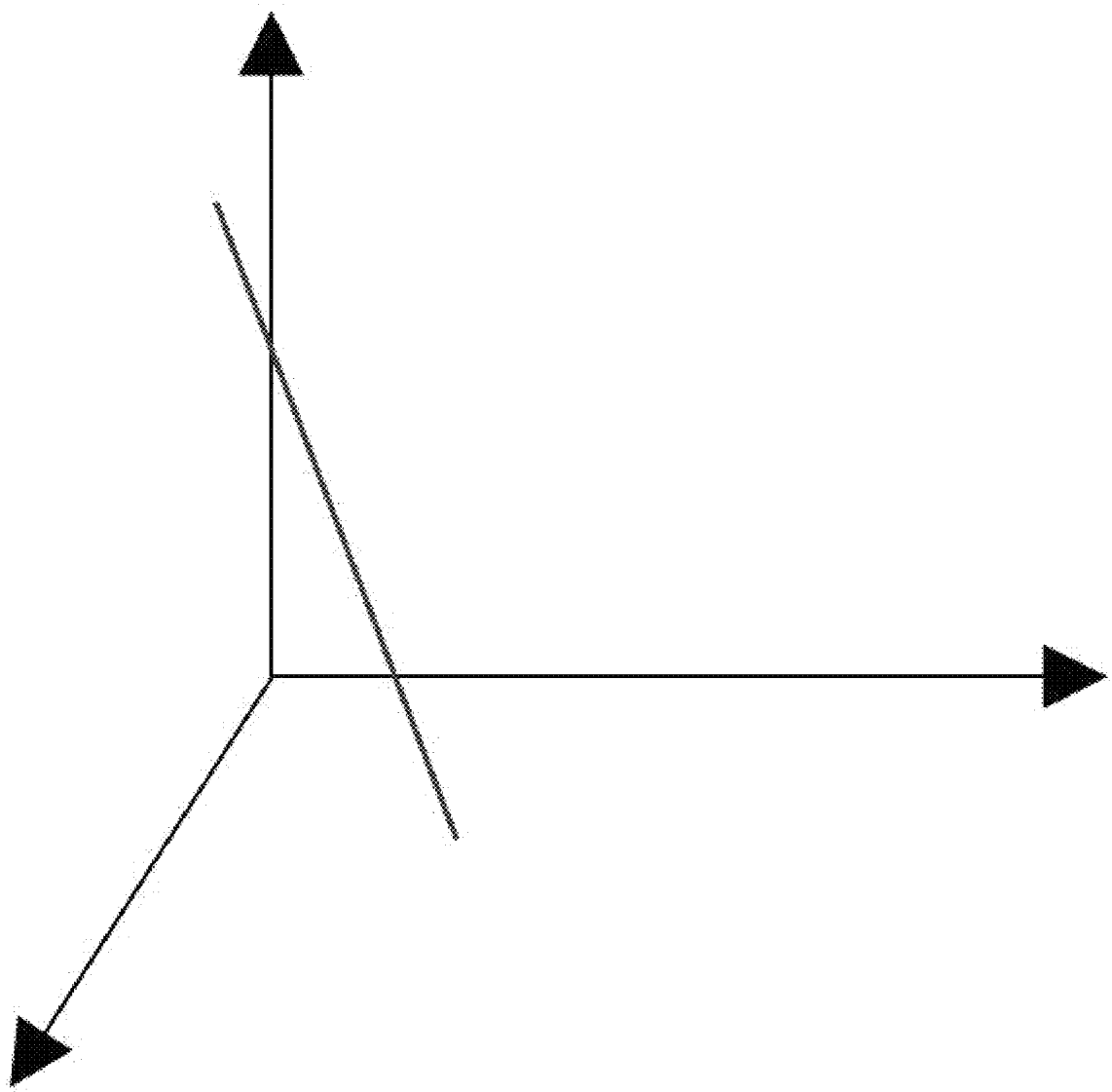
FIG. 11 is a diagram for explaining a three-dimensional optimum line segment search operation according to an embodiment of the present invention.

FIG. 10 is a diagram for explaining a three-dimensional line segment restoration operation according to an embodiment of the present invention, and FIG. 11 is a diagram for explaining a three-dimensional optimum line segment search operation according to an embodiment of the present invention. That is, FIGS. 10 and 11 are diagrams for exemplarily explaining an optimum three-dimensional line segment restoration operation according to an embodiment of the present invention.

Referring to FIGS. 6, 10 and 11, the three-dimensional line segment restoration operation of step S610 (or exemplarily steps S609 and S611) is performed to restore an optimum three-dimensional line segment by using the two-dimensional line segment information and the positional relationship information of the cameras measured in advance. The restored optimum three-dimensional line segments are shown in FIG. 11.

Referring to FIG. 10, in the three-dimensional line segment restoration operation of step S609, information on a predetermined number of two-dimensional line segments is bound (for example, two by two), and then, a plurality of three-dimensional line segments are restored by using the positional relationship information of the cameras measured in advance. FIG. 10 shows three-dimensional line segments.

Referring to FIG. 11, in the three-dimensional optimum line segment search operation of step S611, information on both endpoints of a plurality of three-dimensional line segments is line-fitted again to find the optimum three-dimensional line segments. In this case, as the line fitting algorithm, any algorithm well known in the art may be employed as described above.

Figure 12:
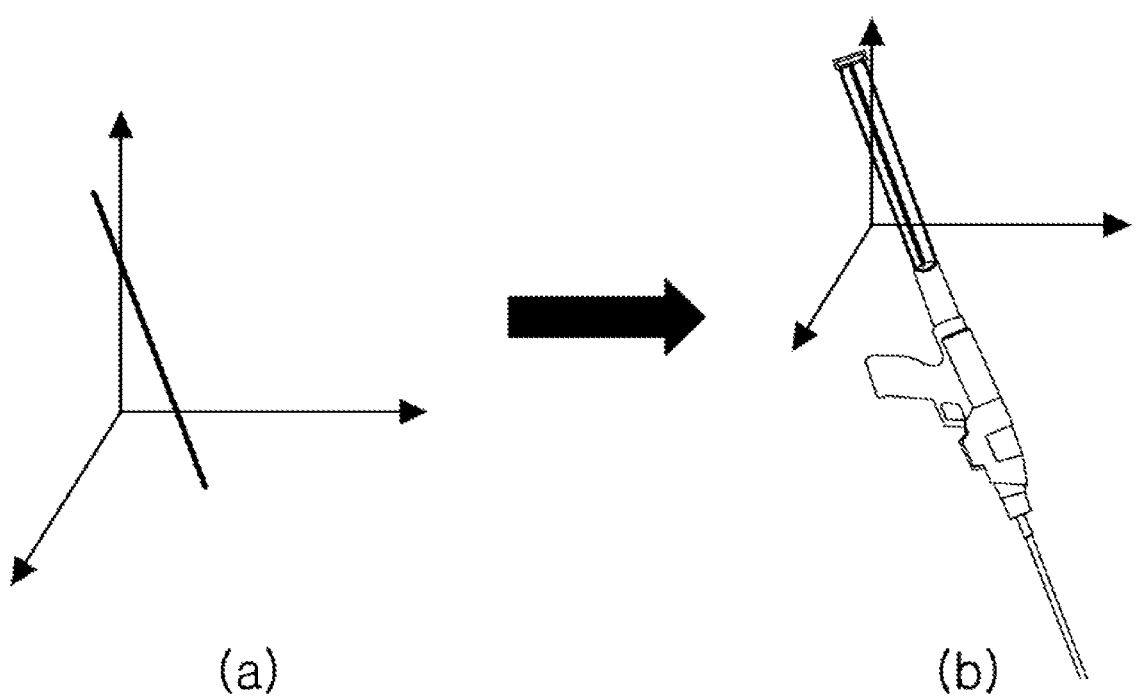
FIG. 12 is a diagram for explaining a posture tracking procedure for the bar type medical device according to an embodiment of the present invention.

FIG. 12 is a diagram for explaining a posture estimation operation for the bar type medical device according to an embodiment of the present invention.

Referring to FIG. 12, in the posture estimation operation of the bar type medical device in step S613, the three-dimensional posture of the actual medical device may be estimated by using the positional relationship between the bar type medical device and the laser beam measured in advance. For example, the laser beam line segment and the needle of the bar type medical device may be set to have the same angle and length while interposing the main body of the medical device (or the lengths of the laser beam line segment and the needle may be set to have a predetermined ratio). In this case, when the position and length of the laser beam line segment are accurately estimated, the position and length of the needle of the bar type medical device can be estimated automatically and accurately.

Figure 13:
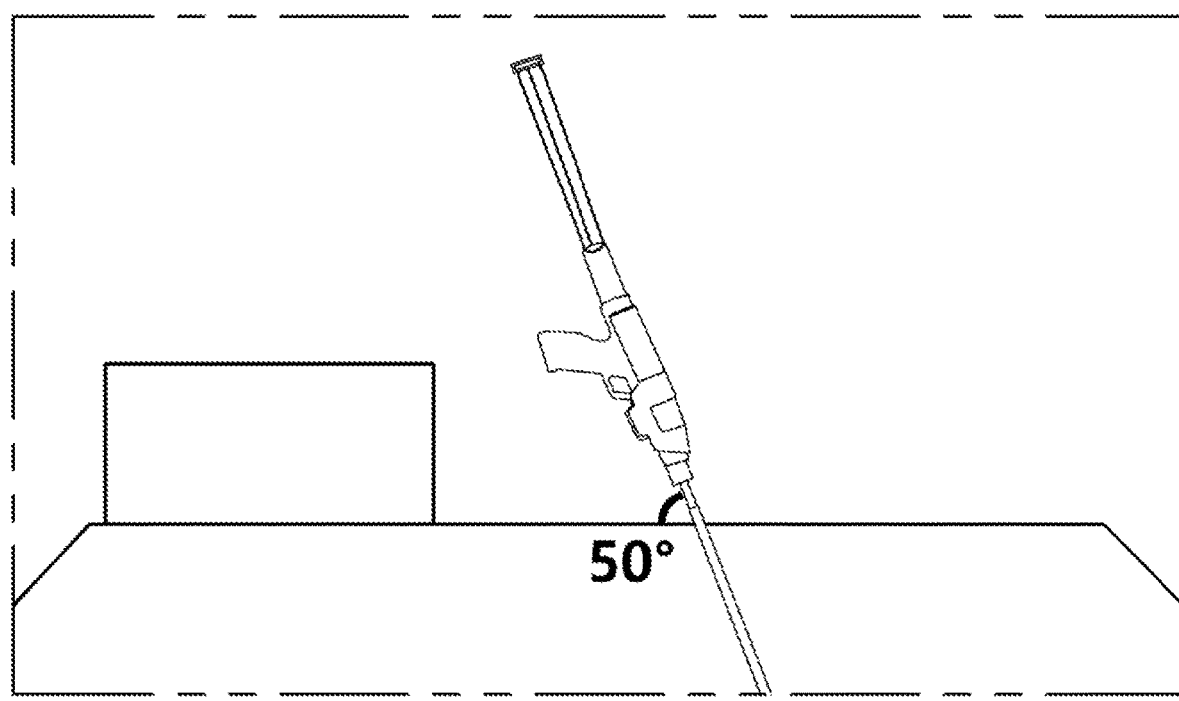
FIG. 13 is a diagram for explaining an operation of visualizing posture information for the bar type medical device according to an embodiment of the present invention.

FIG. 13 is a diagram for explaining visualization of posture information for the bar type medical device according to an embodiment of the present invention.

Referring to FIG. 13, three-dimensional posture information such as the angle and position of the medical device estimated in step 5615 may be displayed on the screen of the display unit 130 in the form of augmented reality. On the screen example of FIG. 13, the bar type medical device is expressed as an augmented object in the form of augmented reality, and an incident angle of the bar type medical device from the parallel line is 50°.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

What is claimed is:

1. A medical device posture tracking system comprising:
a bar type medical device having a bar shape whose front end has a needle or injection shape and whose rear end has an identification line segment extending in a longitudinal direction of the bar shape;
a tracking multi-camera set having a plurality of cameras provided in a plurality of locations to photograph the identification line segment at a plurality of viewpoints;
a display unit configured to display an augmented reality image having the bar type medical device as an augmented object and show related information including a position and angle of the bar type medical device; and
a controller configured to acquire tracking images captured from the tracking multi-camera set in real time for each frame, estimate a three-dimensional line segment by using the acquired images, estimate a three-dimensional posture of the bar type medical device by using the positional relationship between the bar type medical device and the three-dimensional line segment measured in advance, and display the estimated three-dimensional posture including the position and angle information of the bar type medical device on the display unit as the augmented reality image, wherein the bar type medical device has a laser emitting unit for emitting a laser beam at
its rear end, and the laser emitting unit emits the laser beam to form the identification line segment.

2. The medical device posture tracking system according to claim 1, wherein the rear end of the bar type medical device is formed of a transparent material visible from the outside.

3. The medical device posture tracking system according to claim 2, wherein the rear end of the bar type medical device is filled with a medium containing a silver solution or aerogel to make the laser beam visible from the outside.

4. The medical device posture tracking system according to claim 3, wherein a blocking portion formed of a non-transmissive material for preventing the laser beam from leaking to the outside is provided at a tip of the rear end of the bar type medical device.

5. The medical device posture tracking system according to claim 1, wherein the tracking multi-camera set photographs the laser beam.

6. The medical device posture tracking system according to claim 1, wherein the display unit is provided with a rear camera for photographing a rear direction and displays an image photographed from the rear camera and the three-dimensional posture as an augmented reality image in response to a control of the controller.

7. The medical device posture tracking system according to claim 1, wherein the controller performs a camera calibration operation for measuring a positional relationship between each camera of the tracking multi-camera set in advance.

8. The medical device posture tracking system according to claim 7, wherein the controller performs an image cleaning operation for separating the laser beam from the tracking images photographed from the tracking multi-camera set and removing unnecessary noise.

9. The medical device posture tracking system according to claim 8, wherein the controller performs a two-dimensional optimum line segment search operation for searching for an optimum two-dimensional line segment for each image photographed from each camera by using a statistical line fitting algorithm after the image cleaning operation.

10. The medical device posture tracking system according to claim 9, wherein the controller performs an optimum three-dimensional restoration operation by using information on the optimum two-dimensional line segmentsegments and the positional relationship between each camera of the tracking multi-camera set.

11. The medical device posture tracking system according to claim 10, wherein the controller estimates the a-three-dimensional posture of the medical device by using a positional relationship between the bar type medical device and the optimum three-dimensional line segment measured in advance.

12. A medical device posture tracking method by using a medical device posture tracking system having
a bar type medical device having a bar shape whose front end has a needle or injection shape and whose rear end has an identification line segment extending in a longitudinal direction of the bar shape,
a tracking multi-camera set having a plurality of cameras provided in a plurality of locations to photograph the identification line segment at a plurality of viewpoints,
a display unit configured to display an augmented reality image having the bar type medical device as an augmented object and show related information including position and angle information of the bar type medical device, and
a controller configured to perform the medical device posture tracking method,
wherein the bar type medical device has a laser emitting unit for emitting a laser beam at its rear end, and the laser emitting unit emits the laser beam to form the identification line segment,
wherein the method comprising:
acquiring tracking images photographed from the tracking multi-camera set in real time for each frame;
estimating a three-dimensional line segment by using the acquired images;
estimating a three-dimensional posture of the bar type medical device by using the positional relationship between the bar type medical device and the three-dimensional line segment measured in advance; and
displaying the estimated three-dimensional posture including the estimated position and angle information of the bar type medical device on the display unit as the augmented reality image.

13. The medical device posture tracking method according to claim 12, wherein the rear end of the bar type medical device is formed of a transparent material visible from the outside.

14. The medical device posture tracking method according to claim 13, wherein the rear end of the bar type medical device is filled with a medium containing a silver solution or aerogel to make the laser beam visible from the outside.

15. The medical device posture tracking method according to claim 14, wherein a blocking portion formed of a non-transmissive material for preventing the laser beam from leaking to the outside is provided at a tip of the rear end of the bar type medical device .

16. The medical device posture tracking method according to claim 12, wherein the tracking multi-camera set photographs the laser beam.

17. The medical device posture tracking method according to claim 12, wherein the display unit is provided with a rear camera for photographing a rear direction and displays an image photographed from the rear camera and the three-dimensional posture as an augmented reality image in response to a control of the controller.

18. The medical device posture tracking method according to claim 12, further comprising performing a camera calibration operation for measuring a positional relationship between each camera of the tracking multi-camera set in advance.

19. The medical device posture tracking method according to claim 18, further comprising performing an image cleaning operation for separating the laser beam from the tracking images captured from the tracking multi-camera set and removing unnecessary noise.

20. The medical device posture tracking method according to claim 19, further comprising performing a two-dimensional optimum line segment search operation for searching for an optimum two-dimensional line segment for each image photographed from each camera by using a statistical line fitting algorithm after the image cleaning operation.

21. The medical device posture tracking method according to claim 20, further comprising performing an optimum three-dimensional restoration operation by using information on the optimum two-dimensional line segment and the positional relationship between each camera of the tracking multi-camera set.

22. The medical device posture tracking method according to claim 21, further comprising estimating a-the three-dimensional posture of the medical device by using a positional relationship between the bar type medical device and the optimum three-dimensional line segment measured in advance.

\* \* \* \* \*